United States Patent
Hoekstra

[11] Patent Number: 6,066,651
[45] Date of Patent: May 23, 2000

[54] ORALLY-ACTIVE NIPECOTAMIDE GLYCOLAMIDE ESTERS FOR THE TREATMENT OF THROMBOSIS DISORDERS

[75] Inventor: William J. Hoekstra, Villanova, Pa.

[73] Assignee: Ortho-McNeil Pharmaceutical, Inc., Raritan, N.J.

[21] Appl. No.: 09/175,166

[22] Filed: Oct. 20, 1998

Related U.S. Application Data

[60] Provisional application No. 60/063,366, Oct. 29, 1997.

[51] Int. Cl.$^7$ .................. A61K 31/445; C07D 401/12
[52] U.S. Cl. .................. 514/316; 514/318; 514/326; 514/255; 546/189; 546/193; 546/208; 544/360; 544/365
[58] Field of Search .................. 546/189, 193, 546/208; 514/316, 318, 326, 255; 544/360, 365

[56] References Cited

U.S. PATENT DOCUMENTS

| | | | |
|---|---|---|---|
| 5,273,982 | 12/1993 | Alig et al. | 514/315 |
| 5,430,024 | 7/1995 | Alig et al. | 514/18 |
| 5,770,575 | 6/1998 | Beavers et al. | 514/19 |

FOREIGN PATENT DOCUMENTS

| | | |
|---|---|---|
| 0 445 796 B1 | 9/1991 | European Pat. Off. . |
| 0 725 059 A1 | 8/1996 | European Pat. Off. . |
| 95/08536 | 3/1995 | WIPO . |
| WO 95 25091 | 9/1995 | WIPO . |
| 96/29309 | 9/1996 | WIPO . |
| WO 97 33869 | 9/1997 | WIPO . |
| 97/41102 | 11/1997 | WIPO . |

OTHER PUBLICATIONS

Hoekstra W J et al., Design and Evauation of Nonpeptide Fibrinogen Gamma–Chain Based GPIIB/IIIA Antagonists; Jan. 1, 1995; pp. 1582–1592.

Hoekstra WJ et al., Solid Phase Parallel Synthesis Applied to Lead Optimization: Discovery of Potent Analogues of the GPIIB/IIIA Antagonists RWJ–50042; Oct. 22, 1996; pp. 2371–2376.

Hoekstar W J et al., Solid Phase Synthesis Via N–Terminal Attachment to the 2–Chlorotrityl Resin; Apr. 14, 1997; pp. 2629–2632.

Esters of N,N–Disubstituted 2–Hydroxyacetamides as a Novel Highly Biolabile Prodrug Type for Carboxylic Acid Agents; Mar. 1987; pp. 451–454.

*Primary Examiner*—Joseph K. McKane
*Attorney, Agent, or Firm*—Mary A. Appollina

[57] ABSTRACT

Orally-active nipecotamide glycolamide ester derivatives of formula (I):

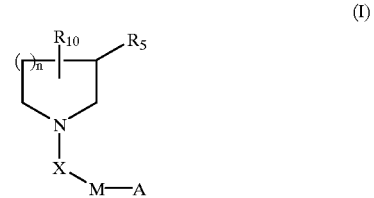

are disclosed as useful in treating platelet-mediated thrombotic disorders.

19 Claims, No Drawings

ORALLY-ACTIVE NIPECOTAMIDE GLYCOLAMIDE ESTERS FOR THE TREATMENT OF THROMBOSIS DISORDERS

CROSS-REFERENCE TO RELATED APPLICATION

This application claims priority from U.S. Ser. No. 60/063366, filed Oct. 29, 1997, the contents of which are hereby incorporated by reference.

BACKGROUND OF THE INVENTION

Platelet aggregation constitutes the initial hemostatic response to curtail bleeding induced by vascular injury. However, pathological extension of this normal hemostatic process can lead to thrombus formation. The final, common pathway in platelet aggregation is the binding of fibrinogen to activated, exposed platelet glycoprotein IIb/IIIa (GPIIb/IIIa). Agents which interrupt binding of fibrinogen to GPIIb/IIIa, therefore, inhibit platelet aggregation. These agents are, therefore, useful in treating platelet-mediated thrombotic disorders such as arterial and venous thrombosis, acute myocardial infarction, unstable angina, reocclusion following thrombolytic therapy and angioplasty, inflammation, and a variety of vaso-occlusive disorders. The fibrinogen receptor (GPIIb/IIIa) is activated by stimuli such as ADP, collagen, and thrombin exposing binding domains to two different peptide regions of fibrinogen: alpha-chain Arg-Gly-Asp (RGD) and gamma-chain His-His-Leu-Gly-Gly-Ala-Lys-Gln-Ala-Gly-Asp-Val (HHLGGAKQAGDV, γ400–411). Since these peptide fragments themselves have been shown to inhibit fibrinogen binding to GPIIb/IIIa, a mimetic of these fragments would also serve as an antagonist. In fact, prior to this invention, potent RGD-based antagonists have been revealed which inhibit both fibrinogen binding to GPIIb/IIIa and platelet aggregation e.g., Ro-438857 (L. Alig, *J. Med. Chem.* 1992, 35, 4393) has an $IC_{50}$ of 0.094 μM against in vitro thrombin-induced platelet aggregation. Some of these agents have also shown in vivo efficacy as antithrombotic agents and, in some cases, have been used in conjunction with fibrinolytic therapy e.g., t-PA or streptokinase, as well (J. A. Zablocki, *Current Pharmaceutical Design* 1995, 1, 533).

The glycolamide ester compounds of the present invention are orally-active GPIIb/IIIa antagonists which exhibit improved oral absorption and in vivo activity over their carboxylic acid congeners. As demonstrated by the results of the pharmacological studies described hereinafter, the compounds show the ability to block fibrinogen binding to isolated GPIIb/IIa ($IC_{50}$'s of ca. 0.0005–0.01 μM), inhibit platelet aggregation in vitro in the presence of a variety of platelet stimuli ($IC_{50}$'s of ca. 0.1–1.0 μM vs. thrombin), and furthermore, inhibit ex vivo platelet aggregation in animal models. Additionally, these agents exhibit efficacy in animal thrombosis models as their progenitors had shown ("Nipecotic Acid Derivatives As Antithrombotic Compounds," application Ser. No. 08-213772, filed Mar. 16, 1994 and "Carboxamide Derivatives of Pyrrolidine, Piperidine, and Hexahydroazepine for the Treatment of Thrombosis Disorders," application Ser. No. 60-016675, filed May 1, 1996). The compounds of the present invention are carboxylic acid glycolamide esters which show efficacy as antithrombotic agents by virtue of their ability to prevent platelet aggregation. Additionally, because the compounds of this invention inhibit integrin-mediated cell-cell or cell-matrix adhesion, they may be useful against inflammation, bone resorption, tumor cell metastasis, etc. (D. Cox, *Drug News & Perspectives* 1995, 8,197).

DISCLOSURE OF THE INVENTION

The present invention is directed to compounds represented by the following general formula (I):

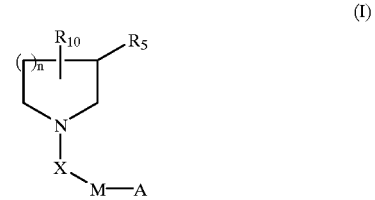

(I)

wherein A, X, M, $R_5$, $R_{10}$, and n are as hereinafter defined. The glycolamide ester compounds of the present invention are orally-active GPIIb/IIIa antagonists which exhibit improved oral absorption and in vivo activity over their carboxylic acid congeners. These platelet aggregation inhibitors are useful in treating platelet-mediated thrombotic disorders such as arterial and venous thrombosis, acute myocardial infarction, reocclusion following thrombolytic therapy and angioplasty, inflammation, unstable angina, and a variety of vaso-occlusive disorders. These compounds are also useful as antithrombotics used in conjunction with fibrinolytic therapy (e.g., t-PA or streptokinase). Pharmaceutical compositions containing such compounds are also part of the present invention.

DETAILED DESCRIPTION OF THE INVENTION

More particularly, the present invention is directed to compounds of the following formula (I):

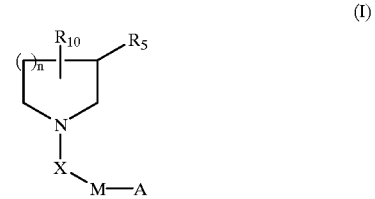

(I)

wherein M is $(CH_2)_m$, CH=CH or C≡C;

A is selected from any of piperidin-2-yl, piperidin-3yl, piperidin-4-yl, piperazin-1-yl, pyrrolidin-2-yl, pyrrolidin-3-yl, $NHR_2$ or

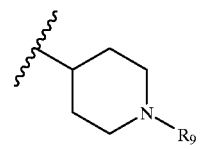

wherein $R_9$ is selected from any of H, alkyl, CH(NH), CMe(NH) or acyl, preferably $R_9$ is hydrogen;

$R_{10}$ is H or $C(O)N(R^1)YZ$, wherein $R^1$ is selected from H or cycloalkyl;

$R_2$ is selected from any of H, alkyl or acyl, preferably $R_2$ is hydrogen;

$R_5$ is H or $C(O)NHQ(CHW)_rCO_2R_8$; wherein Q is selected from $CH_2$, CH-aryl, CH-heteroaryl, CH-substituted-heteroaryl or CH-alkyl; preferably Q is $CH_2$, CH-substituted-heteroaryl or CH-heteroaryl; W is selected from H or $N(R_6)T-R_7$, preferably W is H when Q is CH, and $N(R_6)$-$T$-$R_7$ when Q is $CH_2$; wherein $R_6$ is selected from any of H, alkyl or acyl, preferably $R_6$ is hydrogen; T is selected from C(O), C(N-CN) or $SO_2$, preferably T is C(O); $R_7$ is selected from any of alkyl, aryl, aralkyl, alkoxy, or aminoalkyl; and $R_8$ is H or $CH_2C(O)NR_{11}R_{12}$, preferably $R_8$ is $CH_2C(O)NR_{11}R_{12}$, most preferably $R_8$ is $CH_2C(O)NEt_2$; $R_{11}$ and $R_{12}$ are selected from H, alkyl, or cycloalkyl, preferably $R_{11}$, and $R_{12}$ are alkyl;

m is the integer 1, 2, or 3, preferably m is 1 or 2;

X is selected from any of C(O), C(O)O, C(O)NH, $CH_2$, or $SO_2$;

n is the integer 1, 2, or 3;

r is 0 or 1;

Y is selected from any of $(CH_2)_p$, $CH(R_3)(CH_2)_q$, $(CH_2)_qCH(R^3)$, $(CH(CO_2 R^4)CH_2)_q$, $(CH_2)qCHOH$ or piperidine-3carboxylic acid; with the proviso that when Y is $(CH_2)p$ and p is 2, X is other than C(O) or when X is C(O) then either $R^1$ is other than H or $R_2$ is other than H, and with the proviso that when Y is $(CH(CO_2R^4)CH_2)_q$ X is other than C(O) or $CH_2$, is 2 or 3;

q is 1, 2, or 3, preferably, q is 1;

$R^3$ is alkyl, $C_2$–$C_8$ alkenyl, $C_2$–$C_8$ alkynyl, aryl, aralkyl or heteroaryl;

$R^4$ is H or alkyl or cycloalkyl, preferably $R^4$ is hydrogen;

Z is $CO_2CH_2C(O)NR_{11}R_{12}$; provided that at least one of $R_5$ and $R_{10}$ is hydrogen and $R_5$ and $R_{10}$ are not hydrogen at the same time;

provided that when $R_5$ is $C(O)NHQ(CHW)_rCO_2 R_8$, and Q is CH-heteroaryl or CH-substituted-heteroaryl, and $R_8$ is H, then M is CH=CH;

or the enantiomer or the pharmaceutically acceptable salt thereof.

Preferably, the group $C(O)N(R^1)YZ$ is attached to the ring carbon of the central azacycle at the 3- or 4-position (4-position when larger than a five-membered ring), and most preferably the 3-position.

As used herein, unless otherwise noted alkyl and alkoxy whether used alone or as part of a substituent group, include straight and branched chains having 1–8 carbons. For example, alkyl radicals include methyl, ethyl, propyl, isopropyl, nbutyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. Alkoxy radicals are oxygen ethers formed from the previously described straight or branched chain alkyl groups. Cycloalkyl groups contain 5–8 ring carbons and preferably 6–7 carbons.

The term "aryl", "heteroaryl" or "substituted heteroaryl" as used herein alone or in combination with other terms indicates aromatic or heteroaromatic groups such as phenyl, naphthyl, pyridyl, thienyl, furanyl, or quinolinyl wherein the substituent is an alkyl group. The term "aralkyl" means an alkyl group substituted with an aryl group.

The term "acyl" as used herein means an organic radical having 2–6 carbon atoms derived from an organic acid by removal of the hydroxyl group.

The compounds of the present invention may also be present in the form of a pharmaceutically acceptable salt. The pharmaceutically acceptable salt generally takes a form in which the nitrogen on the 1-piperidine (pyrrolidine, piperazine) substituent is protonated with an inorganic or organic acid. Representative organic or inorganic acids include hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, ptoluenesulfonic, cyclohexanesulfamic, salicylic, saccharinic or trifluoroacetic acid.

Particularly preferred compounds of the present invention include those compounds shown in Table I. Where it is noted, the letter "R" indicates the absolute configuration (Cahn-lngold-Prelog rules).

TABLE I

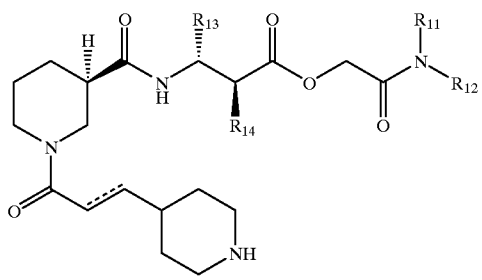

| # | $R_{13}$ | $R_{11}/R_{12}$ | $R_{14}$ |
|---|---|---|---|
| 1 | 3-Pyridyl | Et | H |
| 2 | 3,4-OCH$_2$OPh | Et | H |
| 3 | 5-Bromo-3-pyridyl | Et | H |
| 4 | H | Et | NHCO$_2$CH$_2$Ph |
| 5* | H | Et | NHCO$_2$CH$_2$Ph |
| 6* | H | (CH$_2$)$_5$ | NHCO$_2$CH$_2$Ph |

*Compound contains 4-piperidine-3-propenoyl N-terminus (compounds #1–4 contain 4-piperidine-3-propanoyl N-terminus).

The compounds of the invention wherein $R_{10}$ is H, $R_5$ is $C(O)NHQ(CHW)_rCO_2R_8$, and A is piperidin4-yl, may be prepared as shown in Schemes AA and AB. Enantiomerically-enriched R-(–)nipecotic acid ethyl ester was isolated by chiral resolution of racemic material as its corresponding D-tartaric acid salt (A. M. Akkerman, Rec. Trav. Chim. Pays-Bas 1951, 70, 899), and then converted to Boc-R-nipecotic acid using standard conditions (aq. sodium hydroxide, di-t-butyldicarbonate). Intermediate AA1 was prepared as detailed in provisional U.S. patent application 60-016675 (May 1, 1996) and as published (J. Rico, J. Org. Chem. 1993, 58, 7948). Standard amide bond coupling conditions using AA1, HBTU, HOBT, and Boc-R-nipecotic acid, followed by Boc removal with HCl afforded AA2. Compound AA2 was then acylated with HBTU-activated Boc-4-piperidinepropanoic acid and the resultant methyl ester saponified with lithium hydroxide to give acid AA3. The carboxylate AA3 was then alkylated with 2-chloro-N,N-diethylacetamide/triethylamine in EtOAc, and the Boc group removed with HCl to give final product #1 as its dihydrochloride salt. Compounds #2 and #3 were prepared as shown for #1; resolved β-amino ester starting materials (see Ml experimental) were prepared as shown for AA1.

SCHEME AA

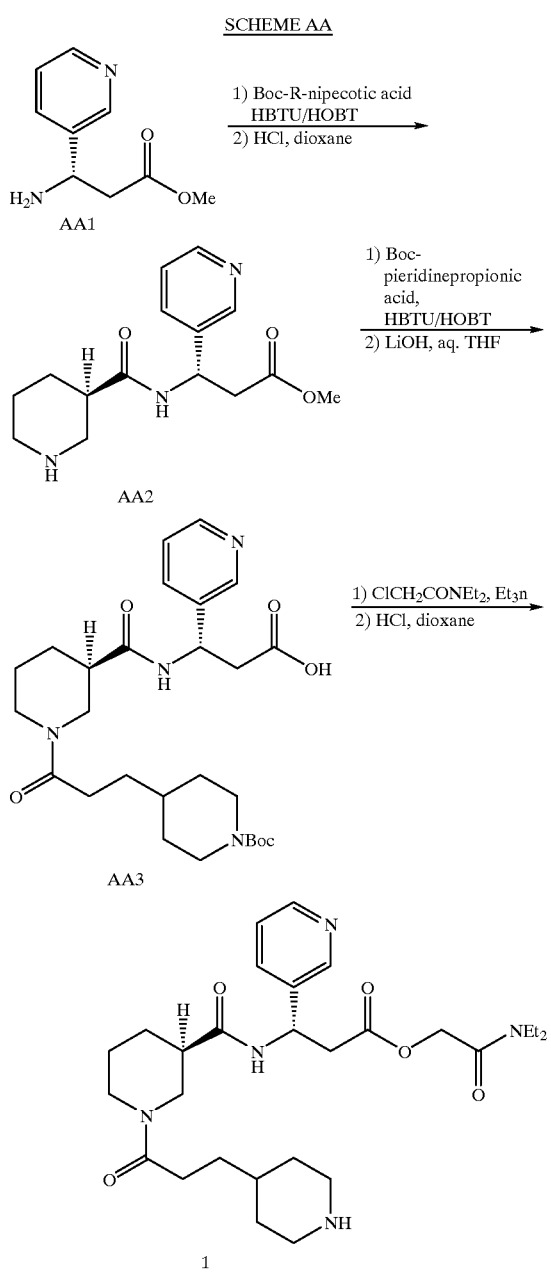

Compound #4 was prepared in a similar manner. Boc-R-nipecotic acid was coupled with methyl N-α-CBZ-L-diaminopropionate (prepared by MeOH/HCl Fischer esterification of commercially-available Nα-CBZ-L-diaminopropionic acid) and then the Boc group removed with HCl to afford AB2. In this synthetic sequence, acid AB3 was alkylated using 2-chloro-N,N-diethylacetamidelcesium carbonate in DMF, and then converted to #4 with HCl.

SCHEME AB

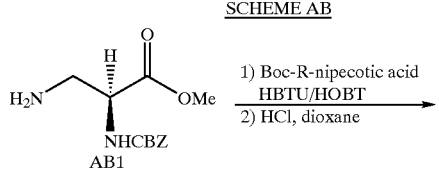

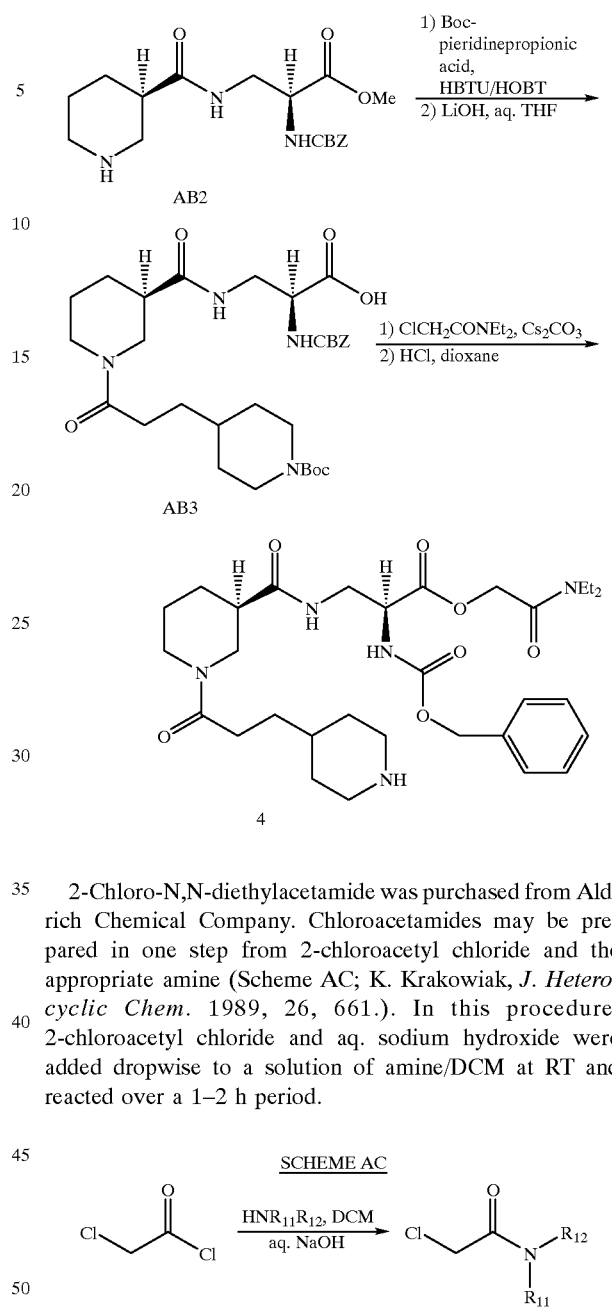

2-Chloro-N,N-diethylacetamide was purchased from Aldrich Chemical Company. Chloroacetamides may be prepared in one step from 2-chloroacetyl chloride and the appropriate amine (Scheme AC; K. Krakowiak, *J. Heterocyclic Chem.* 1989, 26, 661.). In this procedure, 2-chloroacetyl chloride and aq. sodium hydroxide were added dropwise to a solution of amine/DCM at RT and reacted over a 1–2 h period.

SCHEME AC

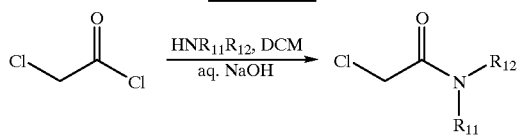

SCHEME AD

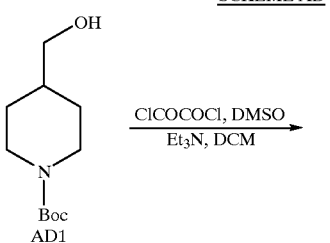

-continued

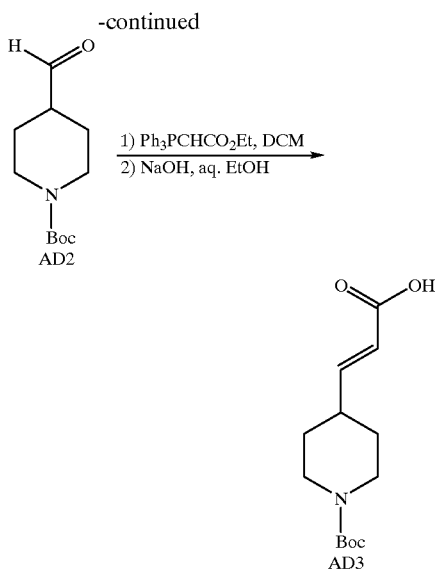

AD2

1) Ph₃PCHCO₂Et, DCM
2) NaOH, aq. EtOH

AD3

Intermediate N-Boc-4-piperidinepropenoic acid AD3 may be prepared as shown in Scheme AD. Alcohol AD1 was oxidized to the corresponding aldehyde AD2 using standard Swern conditions (oxalyl chloride/DMSO). AD2 was converted to the olefinic ester using the Wittig reagent in dichloromethane. This ester was then saponified to the acid in sodium hydroxide to afford AD3. To prepare compound #5, AD3 was coupled with AB2 as described for compound #4 (HBTU/HOBT) and carried forward to final product as shown in Scheme AB.

To prepare the compounds where A is pyrrolidin-2-yl or pyrrolidin-3-yl, intermediate AA2 was acylated with 3-(N-Boc-pyrrolidinyl)propionic acid to produce the acylated derivative using the HBTU acylation procedure. 3-(N-Boc-pyrrolidinyl)propionic acid was synthesized using the methods described in U.S. Pat. No. 4,002,643. Using these procedures, N-Boc-pyrrolecarboxaldehyde (two or three substitution) was treated with sodium hydride/diethyl cyanomethyl-phosphonate in DME to give 3-(N-Boc-pyrrole)acrylonitrile, which was reduced using standard hydrogenolysis conditions ($H_2$, platinum oxide) to afford 3-N-Boc-pyrrolidinyl)propionitrile. The nitrile was then hydrolyzed with aqueous sodium hydroxide to give 3-(N-Boc-pyrrolidinyl)propionic acid (two or three substitution).

To prepare the compounds where A is piperazin-1-yl, intermediate AA2 was acylated with acryloyl chloride/NMM as published (S. G. Gilbreath, *J. Am. Chem. Soc.* 1988, 110, 6172), and the corresponding acrylamide then treated with the appropriate piperazine (e.g. N-methylpiperazine) in refluxing ethanol to give the piperazine product.

To prepare the compounds where A is N-alkyl-piperidine ($R_9$=alkyl), compound #1, for example, was treated with aldehyde/sodium cyanoborohydride in ethanol to give the N-alkylpiperidine. Formamidinopiperidines were prepared by treating ompound #1, for example, with ethyl formimidate•HCl in ethanol; the corresponding acetamidinopiperidines were prepared using S-2-naphthylmethyl thioacetimidate•HCl in ethanol (B. Shearer, *Tetrahedron Lett.* 1997, 38,179).

To prepare the compounds where A is $NHR_2$, intermediate AA2 was acylated with N-Boc-$R_2$aminohexanoic acid, for example, using the standard HBTU coupling conditions cited for example 1.

Compounds where M is ethynyl were prepared by displacement of N-Boc-4 methanesulfonyloxypiperidine with potassium ethyl propiolate (potassium carbonatelethyl propiolate) to give methyl N-Boc-4-piperidineprop-3-ynoate (T. Jeffery, *Tetrahedron Left*. 1989, 30, 2225). This ester was then saponified to the corresponding carboxylic acid and coupled with intermediate AA2 using HBTU.

Compounds where $R_{10}$ is C(O)NR(1)YZ and $R_5$ is H are prepared according to the method described in Scheme M using an appropriately substituted boc-R-nipecotic acid as the starting material.

To prepare the pharmaceutical compositions of this invention, one or more compounds of formula (I) or salt thereof of the invention as the active ingredient, is intimately admixed with a pharmaceutical carrier according to conventional pharmaceutical compounding techniques, which carrier may take a vide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.03 mg to 100 mg/kg (preferred 0.1–30 mg/kg) and may be given at a dosage of from about 0.1–300 mg/kg/day (preferred 1–50 mg/kg/day). The dosages, however, may be varied depending upon the requirement of the patients, the severity of the condition being treated and the compound being employed. The use of either daily administration or post-periodic dosing may be employed.

BIOLOGY

The glycolamide ester compounds of the present invention are orally-active GPIIb/IIIa antagonists which show improved oral absorption and in vivo activity over their carboxylic acid congeners. For instance, compound #4 exhibited >240 min duration in vivo (see Table II) whereas its carboxylic acid congener exhibited 180 min duration at the same oral dose. The compounds interrupt binding of fibrinogen to platelet glycoprotein IIb/IIIa (GPIIb/IIIa) and thereby inhibit platelet aggregation. Such compounds are, therefore, useful in treating platelet-mediated thrombotic disorders such as arterial and venous thrombosis, acute myocardial infarction, reocclusion following thrombolytic therapy and angioplasty, and a variety of vaso-occusive disorders. Because the final, common pathway in normal platelet aggregation is the binding of fibrinogen to activated, exposed GPIIbAlla, inhibition of this binding represents a plausible antithrombotic approach. The receptor is activated by stimuli such as ADP, collagen, and thrombin, exposing binding domains to two different peptide regions of fibrinogen: α-chain Arg-Gly-Asp (RGD) and γ-chain 400–411. As demonstrated by the results of the pharmacological studies described hereinafter, the compounds of the present invention show the ability to block fibrinogen binding to isolated GPIIb/IIIa ($IC_{50}$'s 0.0006–0.005 μM), inhibit platelet aggregation in vitro in the presence of a various of platelet stimuli ($IC_{50}$'s 0.14–1.1 μM vs. thrombin), and furthermore, inhibit ex vivo platelet aggregation in animal models.

IN VITRO SOLID PHASE PURIFIED GLYCOPROTEIN IIB/IIIA BINDING ASSAY.

A 96 well lmmulon-2 microtiter plate (Dynatech-Immulon) is coated with 50 μl/well of RGD-affinity purified GPIIb/IIIa (effective range 0.5–10 μg/mL) in 10 mM HEPES, 150 mM NaCl, 1 mM at pH 7.4. The plate is covered and incubated overnight at 4° C. The GPIIb/IIIa solution is discarded and 150 μl of 5% BSA is added and incubated at RT for 1–3 h. The plate is washed extensively with modified Tyrodes buffer. Biotinylated fibrinogen (25 μl/well) at 2×final concentration is added to the wells that contain the test compounds (25 μl/well). The plate is covered and incubated at RT for 2–4 h. Twenty minutes prior to incubation completion, one drop of Reagent A (Vecta Stain ABC Horse Radish Peroxidase kit, Vector Laboratories, Inc.) and one drop Reagent B are added with mixing to 5 mL modified Tyrodes buffer mix and let stand. The ligand solution is discarded and the plate washed (5×200 μl/well) with modified Tyrodes buffer. Vecta Stain HRP-Biotin-Avidin reagent (50 μl/well, as prepared above) is added and incubated at RT for 15 min. The Vecta Stain solution is discarded and the wells washed (5×200 μl/well) with modified Tyrodes buffer. Developing buffer (10 mL of 50 mM citrate/phosphate buffer @ pH 5.3, 6 mg o-phenylenediamine, 6 μl 30% $H_2O_2$; 50 μl/well) is added and incubated at RT for 3–5 min, and then 2N H2SO4 (50 μl/well) is added. The absorbance is read at 490 nM. The results are shown in Tables II.

IN VITRO INHIBITION OF THROMBIN-INDUCED GEL-FILTERED PLATELET AGGREGATION ASSAY.

The percentage of platelet aggregation is calculated as an increase in light transmission of compound-treated platelet concentrate vs. control-treated platelet concentrate. Human blood is obtained from drug free, normal donors into tubes containing 0.13M sodium citrate. Platelet rich plasma (PRP) is collected by centrifugation of whole blood at 200×g for 10 min at 25° C. The PRP (5 mL) is gel filtered through Sepharose 2B (bed volume 50 mL), and the platelet count is adjusted to 2×107 platelets per sample. The following constituents are added to a siliconized cuvette: concentrated platelet filtrate and Tyrode's buffer (0.14M NaCl, 0.0027M KCI, 0.012M $NaHCO_3$, 0.76 mM $Na_2HPO_4$, 0.0055M glucose, 2 mg/mL BSA and 5.0 mM HEPES @ pH 7.4) in an amount equal to 350 μl, 50 μl of 20 mM calcium and 50 μl of the test compound. Aggregation is monitored in a BIODATA aggregometer for the 3 min following the addition of agonist (thrombin 50 μl 1 unit/mL). The results are shown in Tables II.

TABLE II

| | In Vitro Results | | | |
|---|---|---|---|---|
| | Fibrinogen Binding | | Platelet Aggregation* | |
| Compound # | % Inh. (50 μM) | $IC_{50}$ (μM) | % Inh. (50 μM) | $IC_{50}$ (μM) |
| 1 | 100% | 0.0007 | 100% | 0.14 |
| 2 | 100% | 0.005 | 100% | 1.1 |
| 3 | 100% | 0.0009 | 100% | 0.19 |
| 4 | 100% | 0.0020 | 100% | 0.29 |
| 5 | 100% | 0.0097 | 100% | 0.27 |
| 6 | 100% | 0.0025 | 100% | 0.51 |

*Thrombin-induced aggregation of gel-filtered platelets. NT = not tested.

EX VIVO DOG STUDY

Adult mongrel dogs (8–13 kg) were anesthetized with sodium pentobarbital (35 mg/kg, i.v.) and artificially respired. Arterial blood pressure and heart rate were measured using a Millar catheter-tip pressure transducer inserted in a femoral artery. Another Millar transducer was placed in the left ventricle (LV) via a carotid artery to measure LV end diastolic pressure and indices of myocardial contractility. A lead II electrocardiogram was recorded from limb electrodes. Catheters were placed in a femoral artery and vein to sample blood and infuse drugs, respectively. Responses were continuously monitored using a Modular Instruments data aquisition system.

Arterial blood samples (5–9 ml) were withdrawn into tubes containing 3.8% sodium citrate to prepare platelet rich plasma (PRP) and to determine effects on coagulation parameters: prothrombin time (PT) and activated partial thromboplastin time (APTT). Separate blood samples (1.5 ml) were withdrawn in EDTA to determine hematocrit and cell counts (platelets, RBC's and white cells). Template bleeding times were obtained from the buccal surface using a symplate incision devise and Whatman filter paper.

Aggregation of PRP was performed using a BioData aggregometer. Aggregation of whole blood used a Chronolog impedance aggregometer. PT and APTT were determined on either a BioData or ACL 3000+ coagulation analyser. Cells were counted with a Sysmex K-1 000.

Compounds were solubilized in a small volume of dimethylformamide (DMF) and diluted with saline to a final concentration of 10% DMF. Compounds were administered by the intravenous route with a Harvard infusion pump. Doses was administered over a 15 min interval at a constant rate of 0.33 ml/min. Data were obtained after each dose and in 30 min intervals following the end of drug administration. Oral doses were administered as aqueous solutions via syringe.

Compounds caused marked inhibition of ex vivo platelet aggregation responses. Thus, in whole blood, the compounds inhibited collagen-stimulated (or ADP) aggregation in doses of 0.1–10 mg/kg with marked inhibition of collagen stimulated platelet ATP release. In PRP, the compounds also inhibited collagen stimulated platelet aggregaton with marked activity at 0.1–10 mg/kg. Compounds had no measurable hemodynamic effect in doses up to 1 mg/kg, iv. The drugs produce an increase in template bleeding time at 0.1–1 mg/kg with rapid recovery post treatment. No effects on coagulation (PT or APTT) were observed during treatment and platelet, white and RBC counts were unchanged at any dose of the compounds.

The results indicate that the compounds are broadly effective inhibitors of platelet aggregation ex vivo (antagonizing both collagen and ADP pathways) following iv administration of doses ranging from 0.3–1.0 mg/kg or 3 mg/kg orally. The antiaggregatory effects are accompanied by increases in bleeding time at the higher doses. No other hemodynamic or hematologic effects are observed. The results are shown in Table III.

TABLE III

Ex Vivo Dog Study Results

| | Intravenous Dosing | | Oral Dosing | |
|---|---|---|---|---|
| Cmpd # | Dose | Duration* | Dose | Duration* |
| 1 | 0.3 mpk | 60 min | 3 mpk | >180 min |
| 2 | 1.0 mpk | 120 min | 3 mpk | 150 min |
| 3 | NT | NT | 3 mpk | 90 min |
| 4 | 0.1 mpk | 60 min | 3 mpk | >240 min |
| 5 | 0.1 mpk | 60 min | 1 mpk | >240 min |
| 6 | NT | NT | 1 mpk | 150 min |

*Indicates duration of >50% inhibition of collagen-induced ex vivo platelet aggregation. NT = not tested.

EXAMPLES

Protected amino acids were purchased from Aldrich Chemical or Bachem Bioscience Inc. N-α-CBZ-L-diaminopriopionic acid was purchased from Fluka. Enantiomerically-enriched nipecotic acid ethyl ester were isolated by chiral resolution of racemic material as published (A. M. Akkerman, *Rec. Trav. Chim. Pays-Bas* 1951, 70, 899). All other chemicals were purchased from Aldrich Chemical Company, Inc. High field $^1$H NMR spectra were recorded on a Bruker AC-360 spectrometer at 360 MHz, and coupling constants are given in Herz. Melting points were determined on a Mel-Temp II melting point apparatus and are uncorrected. Microanalyses were performed at Robertson Microlit Laboratories, Inc., Madison, N.J. and are expressed in percentage by weight of each element per total molecular weight. In those cases where the product is obtained as a salt, the free base is obtained by methods known to those skilled in the art, e.g. by basic ion exchange purification. Nuclear magnetic resonance (NMR) spectra for hydrogen atoms were measured in the indicated solvent with tetramethylsilane (TMS) as the internal standard on Bruker AM-360 (360 MHz), AM-400 (400 MHz), or AT-300 (300 MHz) spectrometer. The values are expressed in parts per million down field from TMS. The mass spectra (MS) were determined on a Finnigan 3300 spectrometer (methane), using desorption chemical ionization techniques. Unless otherwise noted, the materials used in the examples were obtained from readily available commercial suppliers or synthesized by standard methods known to anyone skilled in the art of chemical synthesis. The substituent groups, which vary between examples, are hydrogen unless otherwise noted. In the Examples and throughout this application, the following abbreviations have the meanings recited hereinafter.

Bn or Bzl=Benzyl
Boc=t-Butoxycarbonyl
BOC-ON=2-(t-Butoxycarbonyloxyimino)-2-phenylacetonitrile
BOP-Cl=Bis(2-oxo-3oxazolidinyl)phosphinic chloride
CBZ=Benzyloxycarbonyl
CP=compound
DCE=1,2-Dichloroethane
DCM=Dichloromethane
DIC=Diisopropylcarbodiimide
DIEA=Diisopropylethylamine
DMAP=4-Dimethylaminopyridine
DMF=N, N-Dimethylformamide
EDC=Ethyl dimethylaminopropylcarbodiimide
EDTA=Ethylenediaminetetraacetic acid
Et$_2$O=Diethyl ether
HBTU=2-(1 H-Benzotriazole-1-yl)-1,1,3,3-tetramethyluronium hexafluorophosphate
HOBT=Hydroxybenzotriazole
i-Pr=Isopropyl
MPK=milligrams per kilogram
NMM=N-Methylmorpholine
Nip=Nipecotyl (unless noted otherwise, racemic at 3-position)
NT=not tested
PPT=precipitate
PTSA=p-Toluenesulfonic acid
RT=room temperature
TFA=Trifluoroacetic acid
Z=Benzyloxycarbonyl The following examples describe the invention in greater detail and are intended to illustrate the invention, but not to limit it.

Methyl (S)-3-amino-3-(3Pyridyl) propionate•2HCl (AA1)

A mixture of 3-pyridinecarboxaldehyde (0.47 mol), EtOH (100 mL), NH$_4$OAc (0.47 mol), and malonic acid (0.70 mol) was heated at reflux for 6 h, cooled, and filtered. The white solid was washed with EtOH and MeOH and dried (E. Profft, *J. Prakt. Chem.* 1965, 30, 18). This solid was dissolved in 2:1 acetone/water (360 mL), treated with triethylamine (0.72 mol) and phenylacetyl chloride (0.36 mol), and stirred for 22 h. The mixture was evaporated and the residue dissolved in water (500 mL) and adjusted to pH 12 (1 N NaOH). The aqueous layer was adjusted to pH 2 (conc. HCl), extracted with Et$_2$O, and evaporated to a white foam. The foam was purified by silica gel chromatography (10% MeOH/DCM) to give racemic 3-phenylacetamido-3-(3-pyridyl)propionic acid. A solution of this compound (0.22 mol) in water (600 mL) at RT was adjusted to pH 7.5 using KOH (3.0 N) and treated with penicillin amidase (91520 units, Sigma). This mixture was stirred for 47 h, acidified to pH 1 with HCl (conc), and the resultant ppt filtered through Celite. The filtrate was extracted with Et$_2$O (3×300 mL), concentrated in vacuo, and treated with MeOH/conc. NH$_4$OH (9:1). This product-containing solution was purified by silica gel chromatography (eluent DCM/MeOH/NH$_4$OH, 78:18:4) to give (S)-3-phenylacetamido-3-(3-pyridyl) propionic acid ammonium salt (19.5 g, 58%). This product was treated with HCl (6.0 N, 292 mL), heated at reflux for 5 h, cooled to RT, and extracted with Et$_2$O (3×200 mL). The aqueous layer was adjusted to pH 12, concentrated in vacuo, and the resultant solid triturated with MeOH (2×300 mL). This solution was evaporated to give ca. 14 g sodium salt. This material was treated with MeOH (500 mL), 2,2-dimethoxypropane (44 mL), and HCl (4 N in dioxane, 84 mL), and stirred for 90 h at RT. This mixture was filtered and the filtrate concentrated in vacuo. The resultant off-white solid was triturated with Et$_2$O (2×150 mL) and dried to give compound AA1 (16.7 g, 96% ee) as a white, amorphous solid.

Example 1

N-3-(4-Piperidinelropionyl)-R-(−)-nipecotyl-[(S)-3-amino-3-(3-pyridyl]propionic acid 2-(Diethylamino)-2-oxoethyl ester•2HCl (1)

To a mixture of Ml•2HCl (2.0 g, 8.0 mmol), MeCN (120 mL), Boc-R-nipecotic acid (1.8 g), and HOBT (1.1 g) at 5° C. was added NMM (2.6 mL) and HBTU (3.5 g). The mixture was stirred for 20 h, diluted with sat'd ammonium chloride (25 mL), and the MeCN evaporated. This mixture was diluted with EtOAc (120 mL) and the layers separated.

The organic layer was dried (sodium sulfate) and evaporated to give a tan foam. The foam was dissolved in dioxane (35 mL) and anisole (1 mL), treated with HCl (25 mL, 4 N in dioxane), and stirred at RT for 2.5 h. The resultant mixture was evaporated and the white foam triturated with Et$_2$O (50 mL) to give 2.8 g AA2. A mixture of compound AA2, MeCN (120 mL), HOBT (1 g), and HBTU (3.3 g) at 5° C. was treated with NMM (2.5 mL) and N-Boc-4-piperidinepropionic acid (1.9 g) and stirred for 4.5 h. The reaction was diluted with sat'd ammonium chloride (30 mL), and the MeCN evaporated. This mixture was diluted with EtOAc (120 mL) and the layers separated. The organic layer was dried (sodium sulfate) and evaporated to give a foam. The foam was purified by silica gel chromatography (0.5% NH$_4$OH/7% EtOH/DCM) to afford a white foam (2.1 g). This foam was dissolved in THF (25 mL), cooled to 5° C., and treated with aq. lithium hydroxide (0.25 g in 35 mL water). The reaction was stirred for 2 h, acidified with citric acid (0.6 g), and extracted with CHC$_3$ (3×50 mL). The combined organics were dried (sodium sulfate) and evaporated to afford AA3 as a white foam (1.9 g). Compound AA3 (1.0 g, 1.9 mmol) was dissolved in EtOAc (50 mL) and triethylamine (0.3 mL) and treated with sodium iodide (0.09 g) and then 2chloro-N,N-diethylacetamide (0.60 mL). This mixture was stirred for 22 h, diluted with sat'd ammonium chloride (30 mL) and EtOAc (100 mL), and the layers separated. The organic layer was dried (sodium sulfate) and evaporated to give a foam. The foam was purified by silica gel chromatography (0.5% NH$_4$OH/8% EtOH/DCM) to afford a glass (0.56 g). The glass was dissolved in dioxane (25 mL) and anisole (0.5 mL), treated with HCl (15 mL, 4 N in dioxane), and stirred at RT for 4 h. The resultant mixture was evaporated and the white foam triturated with Et$_2$O (50 mL) to give 1 as a white amorphous solid (0.23 g): mp 93–100° C. $^1$H NMR (DMSO-d$_6$) δ 8.9 (m, 3 H), 8.6 (m, 2 H), 8.5 (t, 1 H), 8.0 (t, 1 H), 5.4 (m, 1 H), 4.7 (s, 2 H), 4.2 (m, 1 H), 3.7 (m, 2 H), 3.2 (q, 2 H), 3.1 (q, 2 H), 2.8 (m, 4 H), 2.6 (m, 2 H), 2.3 (m,3 H), 1.2–2.0 (m, 13 H), 1.1 (t, 3 H), 0.9 (t, 3 H); MS m/e 530 (MH$^+$). Anal. calcd. for C$_{28}$H$_{43}$N$_5$O$_5$•2.3 HCl•1.3 Dioxane (729.68): C,52.67; H, 7.69; N, 9.59; Cl, 11.18. Found: C, 52.83; H, 7.99; N, 9.02; Cl, 11.53.

Example 2

N-3-(4-Piperidinepronionyl)-R-(–)-nirecotyl-[(S)-3-amino-3-(3,4-methylenedioxyrheny)] propionic acid 2-(Diethylamino)-2-oxoethyl ester•HCl (2)

Compound 2 was prepared as described in example 1 starting with methyl (S)-3-amino-3-(3,4-methylenedioxyphenyl)propionate•HCl (2.2 g), and isolated as a white powder (0.70 g): $^1$H NMR (CDCl$_3$) δ 9.2 (m, 1 H), 8.8 (m, 1 H), 8.4 (d, 1 H), 6.8 (m, 3 H), 5.91 (s, 2 H), 5.4 (m, 1 H), 4.8 (m, 2 H), 4.3 (m, 1 H), 3.7 (m, 1 H), 3.1–3.5 (m, 5 H), 2.6–3.0 (m, 4 H), 2.4 (m, 3 H), 1.6–2.0 (m, 7 H), 1.2–1.5 (m, 7 H), 1.1 (q, 3 H), 0.9 (t, 3 H); MS m/e 573 (MH$^+$). Anal. calcd. for C$_{30}$H$_{44}$N$_4$O$_7$•1.7 TFA•0.5 H$_2$O (775.55): C, 51.73; H, 6.07; N, 7.22; F, 12.49; KF, 1.16. Found: C, 51.75; H, 6.23; N, 7.13; F, 12.35; KF, 1.12.

Example 3

N-3-(4-Piperidinepropionyl)-R-(–)-nipecotyl-[(S)-3-amino-3-(5-bromo-3-pyridyl]propionic acid 2(Diethylamino)-2-oxoethyl ester•2HCl (3)

Compound 3 was prepared as described in example 1 starting with methyl (S)-3-amino-3-(5-bromo-3-pyridyl) propionate•2HCl (2.9 g), and isolated as a white foam (0.40 g): mp 63–69° C. $^1$H NMR (DMSO-d$_6$) δ 8.8 (m, 3 H), 8.55 (s, 1 H), 8.48 (s, 1 H), 8.4 (m, 1 H), 8.0 (m, 1 H), 5.2 (m, 1 H), 4.72 (s, 2 H), 3.9 (m, 1 H), 3.2 (m, 6 H), 2.9 (m, 2 H), 2.7 (m, 2 H), 2.2 (m, 2 H), 1.9 (m, 3 H), 1.2–1.8 (m, 12 H), 1.1 (t, 3 H), 1.0 (t, 3 H); MS m/e 608 and 610 (MH$^+$). Anal. calcd. for C$_{28}$H$_{42}$BrN$_5$O$_5$•2.1 HCl•1.0 H$_2$O•0.5 Dioxane (747.23): C, 48.22; H, 6.76; N, 9.37; Cl, 9.96. Found: C, 48.01; H, 6.97; N, 9.13; Cl, 10.28.

Example 4

N-3-(4-Piperidineprogionyl)-R-(–)nipecotyl-[(S)-2benzyloxycarbonylamino-3-amino]propionic acid 2-(Diethylamino)-2-oxoethyl ester•HCl (4)

To a mixture of AB1•2HCl (12.2 g, 42 mmol), MeCN (300 mL), Boc-R-nipecotic acid (9.7 g), and HOBT (5.8 g) at 5° C. was added NMM (9.3 mL) and HBTU (15.9 g). The mixture was stirred for 24 h at 5° C., diluted with sat'd ammonium chloride (50 mL), and the MeCN evaporated. This mixture was diluted with EtOAc (300 mL) and the layers separated. The organic layer was washed with sat'd sodium bicarbonate (50 mL), dried (magnesium sulfate), evaporated, and purified by silical gel chromatography (1.5% MeOH/DCM) to give a white foam (14.8 g). The foam was dissolved in dioxane (30 mL), treated with HCl (30 mL, 4 N in dioxane), and stirred at RT for 2 h. The resultant mixture was evaporated and the white foam triturated with Et$_2$O (50 mL) to give AB2 (13 g). A mixture of compound AB2 (6.3 g), MeCN (200 mL), HOBT (2.1 g), and HBTU (5.9 g) at 5° C. was treated with NMM (5.2 mL) and N-Boc-4-piperidinepropionic acid (4.0 g) and stirred for 22 h. The reaction was diluted with sat'd ammonium chloride (40 mL), and the MeCN evaporated. This mixture was diluted with EtOAc (120 mL) and the layers separated. The organic layer was washed with sat'd sodium bicarbonate (30 mL), dried (magnesium sulfate), evaporated, and purified by silical gel chromatography (2.5% MeOH/DCM) to give a foam (7.7 g). 2.5 g of this foam was dissolved in THF (15 mL), cooled to 5° C., and treated with aq. lithium hydroxide (0.17 g in 30 mL water). The reaction was stirred for 2.5 h, acidified with acetic acid (1 mL), and extracted with CHCl$_3$ (3×50 mL). The combined organics were dried (magnesium sulfate) and evaporated to afford AB3 as a white foam (2.1 g). Compound AB3 (1.0 g, 1.9 mmol) was dissolved in DMF (20 mL), water (5 mL), and cesium carbonate (1.0 g), and treated with 2-chloro-N,N-diethylacetamide (2.1 mL). This mixture was heated at 75° C. for 22 h, cooled to RT, concentrated in vacuo, and diluted with DCM (60 mL). This mixture was washed with water (25 mL), dried (magnesium sulfate), and evaporated to give a foam. The foam was purified by silica gel chromatography (4% MeOH/DCM) to afford a glass (1.6 g). The glass was treated with HCl (10 mL, 4 N in dioxane), and stirred at RT for 1.5 h to give a ppt. The HCl was decanted and the ppt triturated with Et$_2$O (50 mL) and dried to afford 4 as a white amorphous solid (0.95 g): mp 57–61° C. $^1$H NMR (DMSO-d$_6$) δ 8.9 (m, 1 H), 8.6 (m, 1 H), 8.1 (m, 1 H), 7.7 (t, 1 H), 7.3 (m, 5 H), 5.05 (s,2 H), 4.8 (m, 2 H), 4.2 (m, 1 H), 3.8 (m, 1 H), 3.1–3.4 (m, 6 H), 2.7 (m, 3 H), 2.3 (m, 2 H), 1.2–1.9 (m, 16 H), 1.1 (t, 3 H), 1.0 (t, 3 H); MS m/e 602 (MH$^+$). Anal. calcd. for C$_{31}$H$_{47}$N$_5$O$_7$•1.2 HCl•1.7 H$_2$O (676.12): 55.07; H, 7.69; N, 10.36; Cl, 6.29. Found: C, 54.86; H, 7.72; N, 10.39; Cl, 6.11.

N-t-Butoxycarbonyl-4-piperidine-3-propenoic acid (AD3)

To a solution of oxalyl chloride (24.8 mL, 50 mmol) in DCM (200 mL) at –78° C. was added DMSO (7.0 mL) dropwise. The mixture was stirred for 30 min, treated with AD1 (8.2 g, 38 mmol), and stirred for 2 h. Triethylamine (31.7 mL) was added dropwise, the mixture was warmed to RT, and the mixture diluted with water (30 mL). The layers were separated; the organic layer was washed with sat'd ammonium chloride (30 mL) and sat'd sodium chloride (30 mL), dried (magnesium sulfate), evaporated, and purified by silica gel chromatography (20% EtOAc/hexane) to give AD2 (7.3 g, 34 mmol) as a white solid. A solution of ethyl 2-(triphenylphosphoranylidene)acetate (13.1 g, 38 mmol) and DCM (40 mL) at 5° C. was treated with AD2 (7.3 g), warmed to RT, stirred for 2.5 h, and evaporated to dryness. This solid was treated with pentane (50 mL), and triphenylphosphine oxide removed by filtration. The pentane solution was concentrated and the solid purified by silica gel chromatography (10% EtOAc/hexane) to afford a glass (8.4 g). The glass was dissolved in EtOH (60 mL) and this solution treated with water (60 mL) and sodium hydroxide (59 mL, 1.0 N) at RT. The mixture was stirred for 4 h, acidified with citric acid (8 g), and extracted with DCM (3×100 mL). The combined organics were dried (magnesium sulfate) and evaporated to give AD3 (7.5 g) as a white solid. MS m/e 256 (MH$^+$).

Example 5

N-3-(4-Piperidinepropenoyl)-R-(−)nipecotyl-[(S)-2-benzyloxycarbonylamino-3-amino]propionic acid 2-(Diethylamino)-2-oxoethyl ester•HCl (5)

Intermediate AD3 (8.5 mmol) and intermediate AB2 (8.5 mmol) were coupled using HBTU/HOBT and the product carried forward to give 5 as described in example 4. Compound 5 was isolated as a white powder (1.6 g): mp 42–45° C. MS m/e 600 (MH$^+$). Anal. calcd. for $C_{31}H_{45}N_5O_7$•1.0 HCl•2.0 $H_2O$ (672.22): C, 55.39; H, 7.50; N, 10.42; Cl, 5.27. Found: C, 55.62; H, 7.37; N, 10.44; Cl, 5.27.

Example 6

N-3-(4Piperidinepropenoyl)-R-(−)nipecotyl-[(S)-2-benzyloxycarbonylamino-3-amino]propionic acid 2-(Piperidino)-2-oxoethyl ester•HCl (6)

Intermediate AD3 (6.2 mmol) and the piperidide derivative of intermediate AB2 (6.2 mmol) were coupled using HBTU/HOBT and the product carried forward to give 6 as described in example 4. Compound 6 was isolated as a white powder (0.94 g): mp 52–56° C. MS m/e 612 (MH$^+$). Anal. calcd. for $C_{32}H_{45}N_5O_7$•1.0 HCl•2.6 $H_2O$ (695.04): C, 55.30; H, 7.42; N, 10.08; Cl, 5.10. Found: C, 55.05; H, 7.39; N, 9.86; Cl, 5.05.

We claim:

1. A compound represented by the general formula (I):

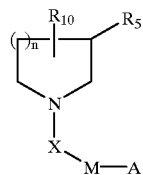

(I)

wherein M is $(CH_2)_m$, CH=CH or C≡C;

A is selected from any of piperidin-2-yl, piperidin-3-yl, piperidin-4-yl, piperazin-1-yl, pyrrolidin-2-yl, pyrrolidin-3-yl, $NHR_2$ or

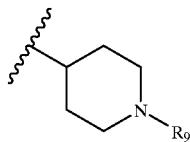

wherein $R_9$ is selected from any of H, alkyl, CH(NH), CMe(NH) or acyl;

$R_{10}$ is H or $C(O)N(R^1)YZ$, wherein $R^1$ is selected from H or cycloalkyl;

$R_2$ is selected from any of H, alkyl or acyl;

$R_5$ is H or $C(O)NHQ(CHW)_rCO_2R_8$; wherein Q is selected from $CH_2$, CH-aryl, CH-heteroaryl, CH-substituted-heteroaryl or CH-alkyl; W is selected from H or $N(R_6)T-R_7$; wherein $R_6$ is selected from any of H, alkyl or acyl; T is selected from C(O), C(N-CN) or $SO_2$; $R_7$ is selected from any of alkyl, aryl, aralkyl, alkoxy, or aminoalkyl; and $R_8$ is $CH_2C(O)NR_{11}R_{12}$, wherein $R_{11}$ and $R_{12}$ are selected from H, alkyl, or cycloalkyl;

m is the integer 1, 2, or 3;

X is selected from any of C(O), C(O)O, C(O)NH, $CH_2$, or $SO_2$;

n is the integer 1, 2, or 3;

r is 0 or 1;

Y is selected from any of $(CH_2)_p$, $CH(R^3)(CH_2)_q$, $(CH_2)_qCH(R^3)$, $(CH(CO_2R^4)CH_2)_q$, $(CH_2)_qCHOH$ or piperidine-3-carboxylic acid; with the proviso that when Y is $(CH_2)_p$ and p is 2, X is other than C(O) or when X is C(O) then either $R^1$ is other than H or $R_2$ is other than H, and with the proviso that when Y is $(CH(CO_2R^4)CH_2)_q$ X is other than C(O) or $CH_2$;

p is 2 or 3;

q is 1, 2, or 3;

$R^3$ is alkyl, $C_2-C_8$ alkenyl, $C_2-C_8$ alkynyl, aryl, aralkyl or heteroaryl;

$R^4$ is H or alkyl or cycloalkyl;

Z is $Ct_2CHC(O)NR_{11}R_{12}$; provided that at least one of $R_5$ and $R_{10}$ is hydrogen and $R_5$ and $R_{10}$ are not hydrogen at the same time;

or the enantiomer or the pharmaceutically acceptable salt thereof.

2. The compound of claim 1 wherein the group $C(O)N(R_1)YZ$ is attached at the 3- or 4-position of the central azacycle.

3. The compound of claim 1 wherein the group $C(O)N(R_1)YZ$ is attached at the 3-position of the central azacycle.

4. The compound of claim 1 wherein $R_5$ is $C(O)NHQ(CHW)_rCO_2R_8$.

5. A compound of claim 1 of the formula:

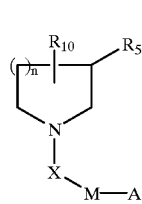

(I)

wherein M is $(CH_2)_m$, CH=CH or C≡C;

A is selected from any of piperidin-2-yl, piperidin-3-yl, piperidin-4-yl, piperazin-1-yl, pyrrolidin-2-yl, pyrrolidin-3-yl, NHR$_2$ or

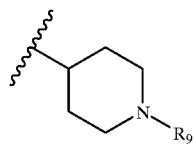

wherein R$_9$ is selected from any of H, alkyl, CH(NH), CMe(NH) or acyl;

R$_{10}$ is H or C(O)N(R$^1$)YZ, wherein R$^1$ is selected from H or cycloalkyl;

R$_2$ is H;

R$_5$ is H or C(O)NHQ(CHW)$_r$CO$_2$R$_8$; wherein Q is selected from CH$_2$, CH-heteroaryl or CH-substituted-heteroaryl; W is selected from H or N(R$_6$)T-R$_7$; wherein R$_6$ is H; T is C(O); R$_7$ is selected from any of alkyl, aryl, aralkyl, alkoxy, or aminoalkyl; and R$_8$ is CH$_2$C(O)NR$_{11}$R$_{12}$; wherein R$_{11}$ and R$_{12}$ are alkyl;

m is the integer 1 or 2;

X is selected from any of C(O), C(O)O, C(O)NH, CH$_2$, or SO$_2$;

n is the integer 1, 2, or 3;

r is 0 or 1;

Y is selected from any of (CH$_2$)$_p$, CH(R$^3$) (CH$_2$)$_q$, (CH$_2$)$_q$CH(R$^3$), (CH(CO$_2$R$^4$)CH$_2$)$_q$, (CH$_2$)$_q$CHOH or piperidine-3-carboxylic acid; with the proviso that when Y is (CH$_2$)$_p$ and p is 2, X is other than C(O) or when X is C(O) then either R$^1$ is other than H or R$^2$ is other than H, and with the proviso that when Y is (CH(CO$_2$R$^4$)CH$_2$)$_q$ X is other than C(O) or CH$_2$;

p is 2 or 3;

q is 1;

R$^3$ is alkyl, C$_2$–C$_8$ alkenyl, C$_2$–C$_8$ alkynyl, aryl, aralkyl or heteroaryl;

R$^4$ is H;

Z is CO$_2$CH$_2$C(O)NR$_{11}$R$_{12}$; provided that at least one of R$_5$ and R$_{10}$ is hydrogen;

or the enantiomer or the pharmaceutically acceptable salt thereof.

6. The compound of claim 5 wherein the group C(O)N(R$^1$)YZ is attached at the 3- or 4-position of the central azacycle.

7. The compound of claim 5 wherein the group C(O)N(R$^1$)YZ is attached at the 3-position of the central azacycle.

8. The compound of claim 5 wherein R$_5$ is C(O)NHQ (CHW)$_r$CO$_2$R$_8$.

9. The compound of claim 1 wherein:

R$_5$ is H or C(O)NHQ(CHW)$_r$CO$_2$R$_8$; wherein Q is selected from CH$_2$, CH-heteroaryl or CH-substituted-heteroaryl; W is selected from H or N(R$_6$)T-R$_7$; wherein R$_6$ is H; T is C(O); R$_7$ is selected from any of alkyl, aryl, aralkyl, alkoxy, or aminoalkyl; and R$_8$ is CH$_2$C(O)NR$_{11}$R$_{12}$; wherein R$_{11}$ and R$_{12}$ are alkyl.

10. The compound of claim 1 of the formula:

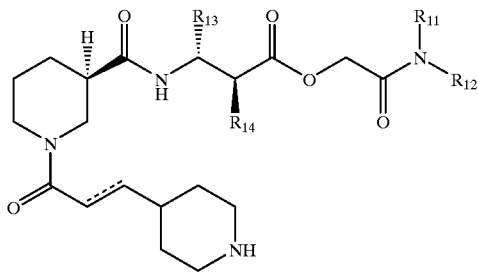

wherein R$_{11}$ and R$_{12}$ are alkyl or taken together are (CH$_2$)$_5$; R$_{13}$ is selected from H, 3-pyridyl, 3,4-OCH$_2$Ph and 3-bromo-3-pyridyl; and R$_{14}$ is selected from H, and NHCO$_2$H$_2$Ph.

11. The compound of claim 1, selected from any of:

N-3-(4-Piperidinepropionyl)-R-(−)-nipecotyl-[(S)-3-amino-3-(3-pyridyl)] propionic acid 2-(Diethylamino)-2-oxoethyl ester•2HCl, N-3-(4-Piperidinepropionyl)-R-(−)-nipecotyl-[(S)-3-amino-3-(3,4-methylenedioxyphenyl)] propionic acid 2-(Diethylamino)-2-oxoethyl ester•2HCl, N-3-(4-Piperidinepropionyl)-R-(−)-nipecotyl-[(S)-3-amino-3-(5-bromo-3-pyridyl)] propionic acid 2-(Diethylamino)-2-oxoethyl ester•2HCl, N-3-(4-Piperidinepropionyl)-R-(−)nipecotyl-[(S)-2-benzyloxycarbonylamino-3-amino]propionic acid 2-(Diethylamino)-2-oxoethyl ester•HCl, N-t-Butoxycarbonyl-4-piperidine-3-propenoic acid, N-3-(4Piperidinepropenoyl)-R-(−)-nipecotyl-[(S)-2-benzyloxycarbonylamino-3-amino]propionic acid 2-(Diethylamino)-2-oxoethyl ester•HCl, and N-3-(4Piperidinepropenoyl)-R-(−)-nipecotyl-[(S)-2-benzyloxycarbonylamino-3-amino]propionic acid 2-(Piperidino)-2-oxoethyl ester•HCl.

12. The compound of claim 1 which is:

N-3-(4-Piperidinepropionyl)-R-(−)-nipecotyl-[(S)-3-amino-3-(3-pyridyl)]propionic acid 2-(Diethylamino)-2-oxoethyl ester.

13. A pharmaceutical composition for treating platelet-mediated thrombic disorders comprising the compound of claim 1 in an effective amount for treating such disorders in combination with a pharmaceutically acceptable carrier.

14. A method of making the composition of claim 13 comprising mixing an effective amount of the compound with a pharmaceutically acceptable carrier.

15. A method of treating platelet-mediated thrombic disorders comprising administering to a patient afflicted with such disorder an effective amount of the compound of claim 1 to treat such disorder.

16. The method of claim 15, wherein the amount is 0.1–300 mg/kg/day.

17. A method of treating platelet-mediated thrombic disorders comprising administering to a patient afflicted with such disorder an effective amount of the composition of claim 13 to treat such disorder.

18. A method of inhibiting platelet aggregation in a patient in need thereof comprising administering to the patient an effective amount of the compound of claim 1.

19. The method of claim 18, wherein the amount is 0.1–300 mg/kg/day.

* * * * *